(12) United States Patent
Gilbert et al.

(10) Patent No.: US 7,695,459 B2
(45) Date of Patent: *Apr. 13, 2010

(54) NASOGASTRIC TUBE INSERTION SYSTEM AND METHOD

(75) Inventors: Paul J. Gilbert, 1650 W. Ogden Ave., #2, Chicago, IL (US) 60612-3234; Robert P. Gilbert, Lutz, FL (US)

(73) Assignee: Paul J. Gilbert, Payson, AZ (US)

( * ) Notice: Subject to any disclaimer, the term of this patent is extended or adjusted under 35 U.S.C. 154(b) by 714 days.

This patent is subject to a terminal disclaimer.

(21) Appl. No.: 11/347,481

(22) Filed: Feb. 3, 2006

(65) Prior Publication Data

US 2006/0189947 A1    Aug. 24, 2006

Related U.S. Application Data

(60) Provisional application No. 60/650,806, filed on Feb. 8, 2005.

(51) Int. Cl.
*A61M 31/00* (2006.01)
(52) U.S. Cl. ............. 604/270; 604/103.04; 604/164.13; 604/165.01
(58) Field of Classification Search ............ 604/103.04, 604/164.13, 165.01, 265, 270, 275
See application file for complete search history.

(56) References Cited

U.S. PATENT DOCUMENTS 2,657,691 A   11/1953  Nordstrom, Jr.
3,395,710 A * 8/1968  Stratton et al. .............. 604/270
4,735,214 A   4/1988  Berman et al.
4,819,619 A * 4/1989  Augustine et al. ....... 128/200.26
4,887,997 A   12/1989  Okada et al.
5,334,167 A * 8/1994  Cocanower ................. 604/523
5,366,444 A * 11/1994  Martin ....................... 604/159
5,391,158 A   2/1995  Peters et al.
2004/0039350 A1* 2/2004  McKittrick ................. 604/270

FOREIGN PATENT DOCUMENTS

JP    2002 191552 A    7/2002

* cited by examiner

*Primary Examiner*—Kevin C Sirmons
*Assistant Examiner*—Elizabeth R Moulton
(74) *Attorney, Agent, or Firm*—Carmen B. Patti; Carmen Patti Law Group, LLC

(57) ABSTRACT

A nasogastric tube insertion system comprises a nasogastric tube, a guide element, and an inserter element. The inserter element has a slim, elongate main body, a handle attached to the body, and an anatomically curved insertion section. The guide element comprises a swallowable weight attached to a cord, string, monofilament line, or other similar line. The nasogastric tube comprises a tube having one or more interior bores or lumina and a guide element capture structure. In use, the swallowable weight is placed onto the end of the inserter element. The inserter element is inserted through the patient's nasal passages and optionally into the oropharynx. The weight is released and the patient swallows it into the stomach. The guide element is threaded through the guide element retaining structure, and the nasogastric tube is safely inserted along the guide element into the patient's stomach. The tube and guide element are removed together when no longer needed.

36 Claims, 12 Drawing Sheets

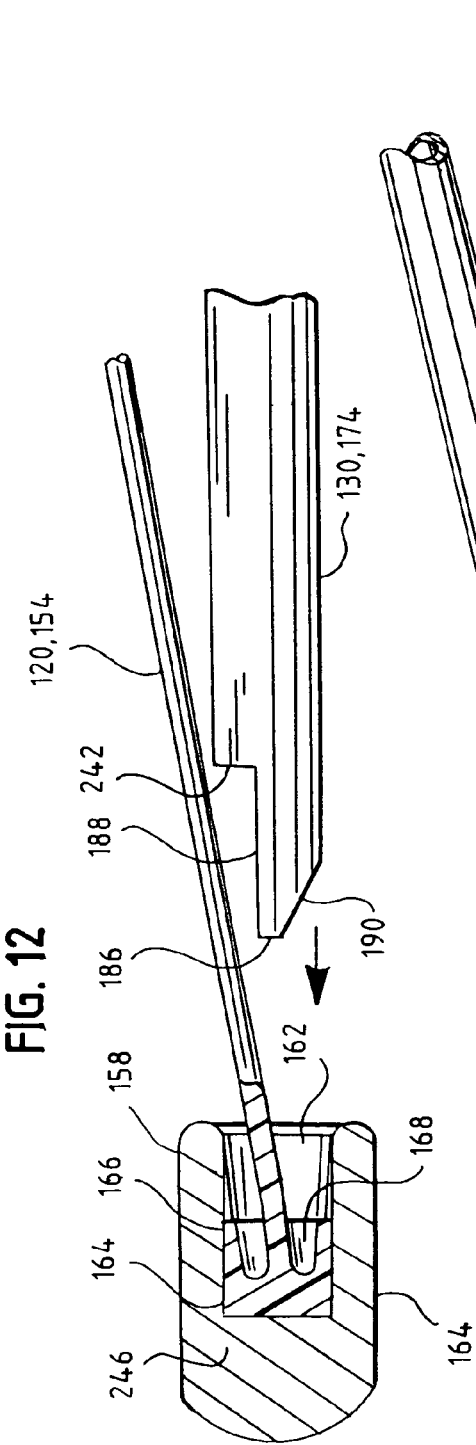
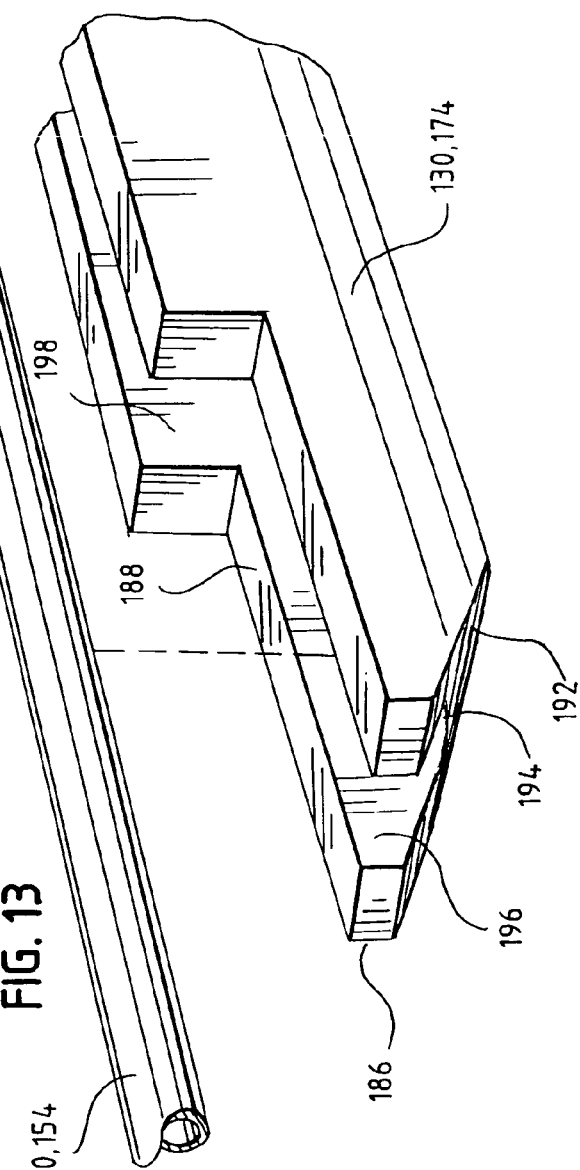

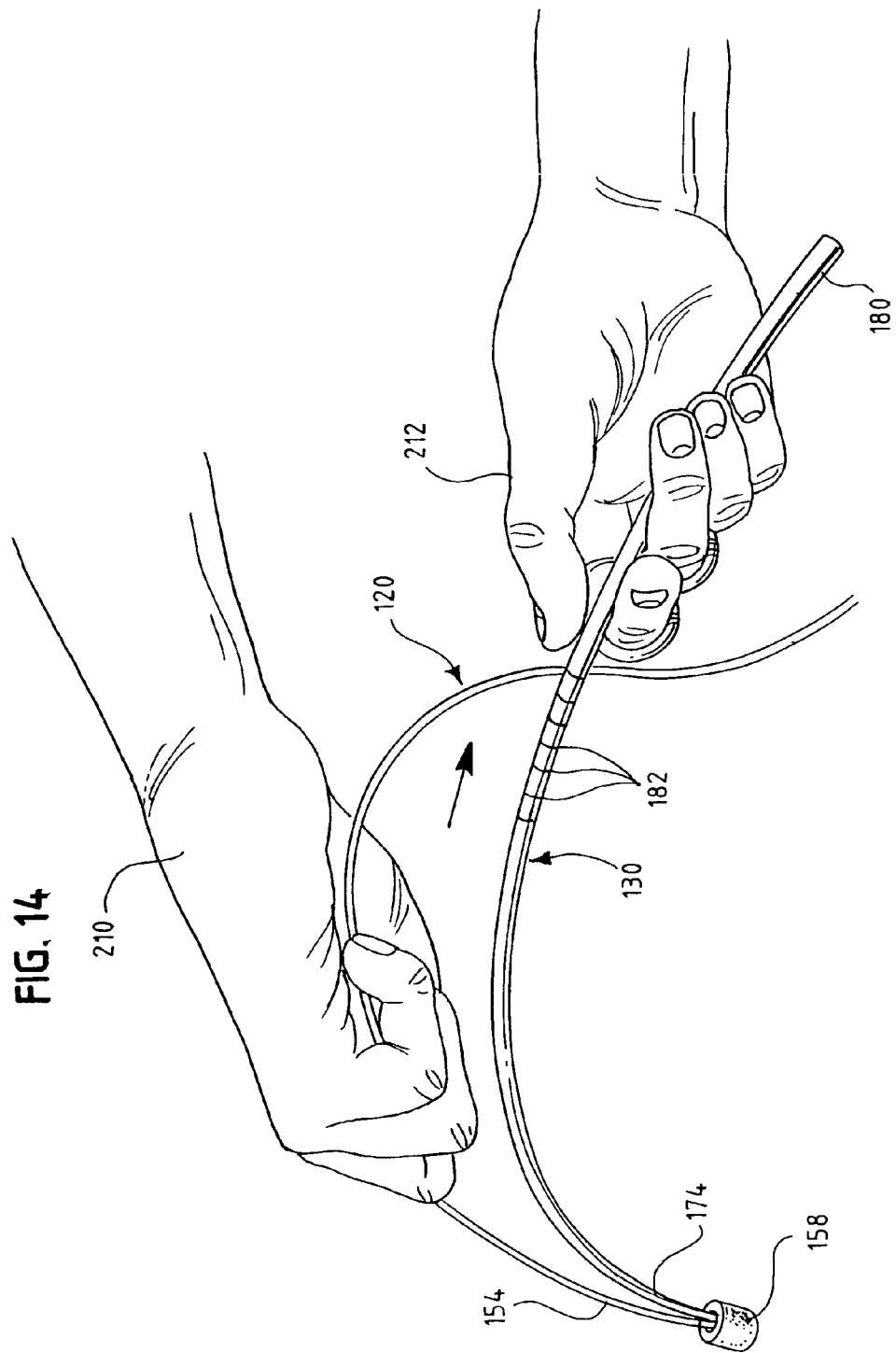

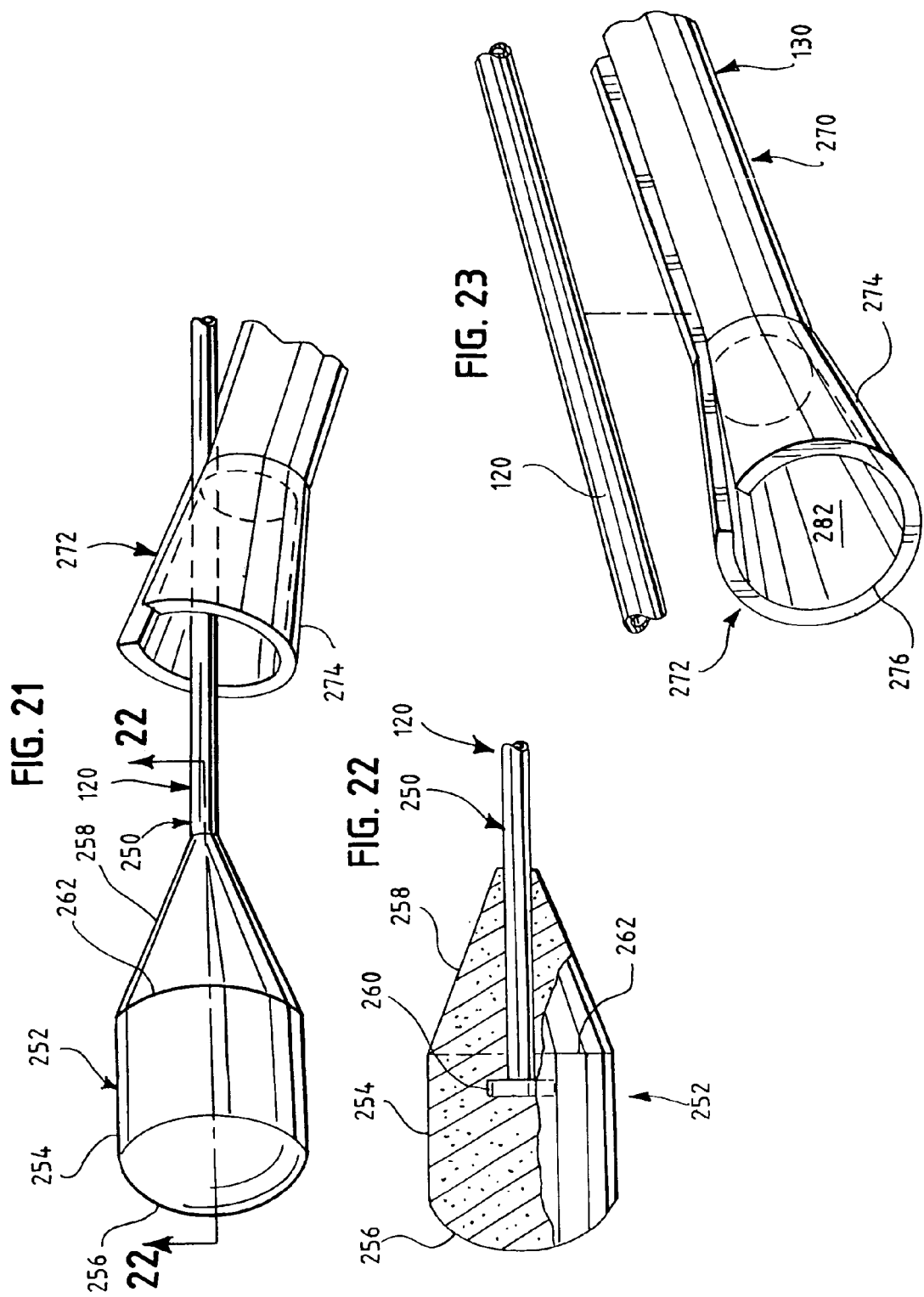

NASOGASTRIC TUBE INSERTION SYSTEM AND METHOD

CROSS-REFERENCE TO RELATED APPLICATIONS

This application claims the benefit under 35 U.S.C. Sec. 119(e) of application No. 60/650,806, filed 8 Feb. 2005.

FIELD OF THE INVENTION

This invention relates to nasogastric tubes, and more particularly to a system and method for inserting a nasogastric tube in a patient.

BACKGROUND OF THE INVENTION

A nasogastric tube is a generally flexible tube inserted through a patient's nasal passages to extend through the esophagus and into the stomach, for the purposes of allowing the introduction of fluids into the stomach, the removal of fluids from the stomach, or both. A nasogastric tube is often used in an emergency situation in an emergency room, trauma center, or immediate care facility. The nasogastric tube is usually inserted by or under the supervision of a physician. There are a number of situations in which the use of a nasogastric tube may be indicated, including, without limitation: upper gastrointestinal bleeding; a bowel obstruction or illeus; ingestion of a poison, contaminant, or drug of inappropriate kind or quantity (i.e., an "overdose"); or when whole bowel irrigation is needed.

Known nasogastric tubes are constructed of a generally flexible material and have one or more separate interior bores or lumina, each extending most of the length of the tube. Kim U.S. Pat. No. 3,999,554 discloses an exemplary nasogastric tube. Plural lumina allow multiple functions, such as the introduction of fluids, removal of fluids, and ventilation of the region around the end of the tube, to be performed simultaneously. The construction of known nasogastric tubes varies, but in general, at one end intended for insertion into the patient, openings are provided to allow communication of fluids, possibly including gases, between the interior lumina and the region surrounding the end of the tube. At the opposite end of the nasogastric tube, separate sockets or tubes are provided for connection to various sources of fluids to be introduced into the patents stomach or to suction to remove fluids or gases from the patient's stomach.

Several significant disadvantages manifested by known nasogastric tubes arise during the process of inserting the nasogastric tube through the patient's nasal passages and into the stomach.

One disadvantage of known nasogastric tubes is the difficulty of safely inserting the nasogastric tube so that it does not incorrectly intubate the patient's trachea and lungs. Conventionally, the nasogastric tube is placed into the patient's nostril and pushed into the back of the oropharynx. The tube is typically lubricated at the tip. In some cases, the back of the oropharynx is numbed with a numbing spray. When the tube is in the oropharynx, the patient is asked to swallow the tube. The tube has some rigidity and cannot be independently swallowed by the patient. Instead, the person inserting the tube assists by pushing the tube into the esophagus and into the stomach while the patient is attempting to swallow.

Because the nasogastric tube is flexible and must undergo a significant bend in the oropharynx, it is impossible to precisely control the position of the end of the tube, and there is considerable risk that the tube will enter the trachea and eventually the lung, instead of the esophagus. Intubating the trachea and lung can have severe consequences, including death. Such intubation may cause damage to vocal cords and airway. It also may cause an extreme coughing and gag response in some patients. In some cases, the patient experiences such discomfort that the patient will not thereafter allow any further attempts at placing the nasogastric tube. In other cases, the patient may tolerate the nasogastric tube even after it has entered the lung, and may even be able to speak. This may cause the healthcare provider to erroneously believe the nasogastric tube has been properly placed in the stomach. If the nasogastric tube is incorrectly placed, and medication is improperly introduced into the lungs instead of the stomach, it could cause extreme morbidity or even death.

The epiglottis covers the trachea during the act of swallowing. The risk of intubating the trachea can be minimized by pushing the tube into the esophagus while the patient is attempting to swallow and entrance to the trachea is blocked by the epiglottis. However, this requires precise timing on the part of the medical professional who is inserting the tube. A further problem is that some patients cannot attempt to swallow because the tube activates their gag reflex. Although the tube is generally flexible, it is rigid compared to tissues of the oropharynx and esophagus, and even when a numbing agent has been used, some patients will gag. Because they are unable to swallow, the epiglottis does not cover the trachea and the nasogastric tube may intubate the trachea and lungs.

Another disadvantage of known nasogastric tubes is that pushing the hard tip of the nasogastric tube through the nasal passage and sinus often causes pain, bleeding, and significant trauma to the nasal cavity. The tube may abrade or irritate the tissues it encounters, particularly where it must bend downward toward the esophagus. In addition, the entire process can cause significant discomfort to the patient.

Other workers in this field have sought to remedy some of these disadvantages. Knott U.S. Pat. No. 5,690,620 discloses an anatomically conforming nasogastric tube having a normally-curved or normally-bent leading end and an additional bend near the leading end. The bent portion of the nasogastric tube is intended to conform to the shape of the soft palate, thereby applying a reduced pressure against the posterior nasopharynx. Knott further discloses a method of inserting the nasogastric tube which involves rotating the tube to bias the bent leading end of the tube in various desired directions so as to avoid obstructions, reliably enter the esophagus, or bias the tip in a particular position with respect to the stomach outlet. However, Knott's apparatus and method do not assure that the leading end of the tube will not encounter, abrade, and irritate tissues during insertion. It also does not resolve the problem that the presence of the tube excites the patient's gag reflex. Moreover, rotating the trailing end of the tube does not ensure that the leading edge of the tube will identically rotate. Therefore, the difficulty of precisely positioning the leading end of the nasogastric tube remains. Thus, the Knott nasogastric tube does not satisfactorily resolve the problems of potentially intubating the trachea and lung, irritating or damaging the nasal cavity, and causing patient discomfort.

Peters U.S. Pat. No. 5,391,158 discloses a system for introducing a nasogastric tube into the stomach of a patient. The Peters system includes a digestible weight to be swallowed by the patient, and a digestible guide string having one end attached to the weight. The nasogastric tube is telescoped around the guide string; during the tube's insertion it follows the guide string into the patient's stomach. Peters discloses that the digestible weight is inserted through the patient's nostril to the nasopharynx. However, Peters does not disclose how the weight is propelled to the nasopharynx, and it is believed this presents a significant difficulty in using the device. In addition, in many instances in which a nasogastric tube is needed, the patient's digestive system is not functioning properly. It is dangerous to assume that the "digestible" weight and guide string can actually be digested. The use of a "digestible" weight and string could even aggravate the patient's condition, and may cause other complications. Thus, the Peters nasogastric tube and insertion system also does not satisfactorily resolve the aforementioned disadvantages of known nasogastric tubes.

There has remained a need in the art for a nasogastric tube which can be safely inserted into the patient, which minimizes risk of intubating the trachea and lungs, which avoids damage to the oropharynx, the esophagus, and other tissues, and which minimizes patient discomfort during insertion.

OJBECT AND SUMMARY OF THE INVENTION

It is therefore an object of the present invention to minimize the aforementioned disadvantages of known nasogastric tubes.

A nasogastric tube insertion system constructed according to an aspect of the present invention includes an inserter element, a guide element, and a nasogastric tube.

The function of the inserter element is to aid in the initial placement of a portion of the guide element in the patient's oropharynx. The inserter element is constructed as a generally thin, longitudinal member having predominantly straight main body section and a curved insertion section. A handle attached to and extending downward from the main body allows the inserter to be readily grasped and controlled by a user. The insertion section has one or more curved portions such that it generally conforms to the anatomy of a typical patient's nasal passages and oropharynx; the curved portions may have a total curvature in the range of approximately 70 to 100 degrees of arc in the direction of the handle. A section extending rearward of the main body section improves stability during handling of the device. The inserter element includes markings to allow the user to readily ascertain when a predetermined insertion depth has been reached. The tip of the insertion section may have a stepped portion of reduced thickness for loosely engaging the swallowable weight of the guide element. Alternatively, the tip of the insertion section may have a conical-concave shape for receiving and loosely engaging a portion of the swallowable weight.

The function of the guide element is to establish a desired path for passage of nasogastric tube through the patient's nasal passages, the oropharynx, the esophagus, and the stomach, and to guide the nasogastric tube along that path during the tube's insertion. The guide element is constructed as a generally longitudinal thin cord or line having a leading section of sufficient flexibility to be easily inserted into and swallowed by the patient, and a trailing section of sufficient rigidity to guide the nasogastric tube 110 as the tube is inserted. The trailing section also functions as a tether. A swallowable weight is attached to the leading section. The longitudinal portion of the guide element may be constructed as a unitary or monofilament line or piece, but may also be constructed as a string or cord, or a similar form of stranded or woven multifilament line. The swallowable weight may be constructed of a resilient, spongiform outer shell, with an interior structure, such as a cup, or anchor, for affixing the shell to the longitudinal portion of the guide element. The outer shell may be absorbent, in order to absorb a numbing agent or a vasoconstricting agent, and may, for example, be constructed from an open-cell foam.

The nasogastric tube is constructed as a generally slender tube having one or more interior bores or lumina extending along the length of tube for conducting fluids or gases between the patient's stomach and external sources, receptacles, or the atmosphere. The nasogastric tube has a leading end intended for insertion into the patient. A guide element retaining structure is provided near the leading end of the tube. The retaining structure has an eye or lumen for accepting the guide element and is arranged to allow the retaining structure, and the nasogastric tube in general, to slide along the guide element. The leading end of the nasogastric tube has one or more openings coupling the interior bores or lumina to the outside. The proximal end of the nasogastric tube also includes openings into the interior bores or lumina. Alternatively, the proximal end of the nasogastric tube may break out into one or more separate connection tubes coupled to the interior bores or lumina. The openings and connection tubes accommodate connection to fluid sources, vacuum "supplies," or the atmosphere, such that fluids and medications can be introduced into or removed from the patient's stomach, and may also allow gasses to be vented.

According to another aspect of the invention, a method for inserting a nasogastric tube includes the steps of attaching the swallowable weight to the tip of the inserter element; optionally applying a numbing or vasoconstricting agent to the swallowable weight; inserting the inserter element through the patient's nasal passages for a predetermined distance, thereby placing the swallowable weight in an expected location, which may be the patient's oropharynx; releasing the weight from the tip of the inserter element; optionally extending the guide element a further distance into the nasal passage or oropharynx; withdrawing the inserter element; having the patient swallow the weight, thereby placing the weight into the patient's stomach; optionally threading the free end of the guide element through an opening of the guide element retaining structure of the nasogastric tube; and inserting the nasogastric tube through the patient's nasal passages and into the patient's stomach along the guide element, thereby following the path established by the guide element. The weight and guide element remain in the patient's stomach until they and the nasogastric tube are withdrawn together. The steps of attaching the swallowable weight to the tip of the inserter element and threading the free end of the guide element through an opening of the guide element retaining structure may be performed as a part of the process of manufacturing the nasogastric tube insertion system rather than as part of the insertion process.

BRIEF DESCRIPTION OF THE DRAWINGS

These and other features of this invention will be best understood by reference to the following detailed description of a preferred embodiment of the invention, taken in conjunction with the accompanying drawings, in which:

FIG. 12 is an enlarged side view of the insertion section 174 of inserter element 130 of FIGS. 1 and 11 and the leading section 154 of guide element 120 of FIGS. 1-4 showing the insertion section 174 about to be attached to the guide element 120;

FIG. 13 is an enlarged perspective view of the tip 186 of insertion section 174 of inserter element 130 of FIGS. 1, 11, and 12 and a portion of the leading section 154 of guide element 120 of FIGS. 1-4;

FIG. 14 is a side view showing the guide element 120 of FIGS. 1-4 attached to the inserter element 130 of FIGS. 1, 11, and 12, and depicting a stage in an exemplary method of inserting the nasogastric tube insertion system 100 in which the swallowable weight 158 is held on the tip 186 of inserter element 130 by tension on the guide element 120 provided by the user;

FIG. 21 is an enlarged side view of an alternative embodiment 270 of the insertion section of inserter element 130 of FIGS. 1 and 11 and an alternative leading section 250 of guide element 120 of FIGS. 1-2, showing the alternative insertion section 270 about to be attached to the guide element 120;

FIG. 22 is an enlarged cross-section view of an alternative embodiment 250 of the leading section of the guide element 120 of FIG. 21, taken along the section line 22-22 thereof; and FIG. 23 is an enlarged perspective view of the tip 272 of alternative insertion section 270 of inserter element 130 of FIGS. 1 and 21 and a portion of the alternative leading section 250 of guide element 120 of FIG. 22.

DETAILED DESCRIPTION OF THE PREFERRED EMBODIMENT

A preferred embodiment of nasogastric tube insertion system 100 constructed according to the present invention is shown generally in FIGS. 1-20. The nasogastric tube insertion system 100 is intended for use with a patient who is conscious, alert, and able to swallow.

Figure 1:
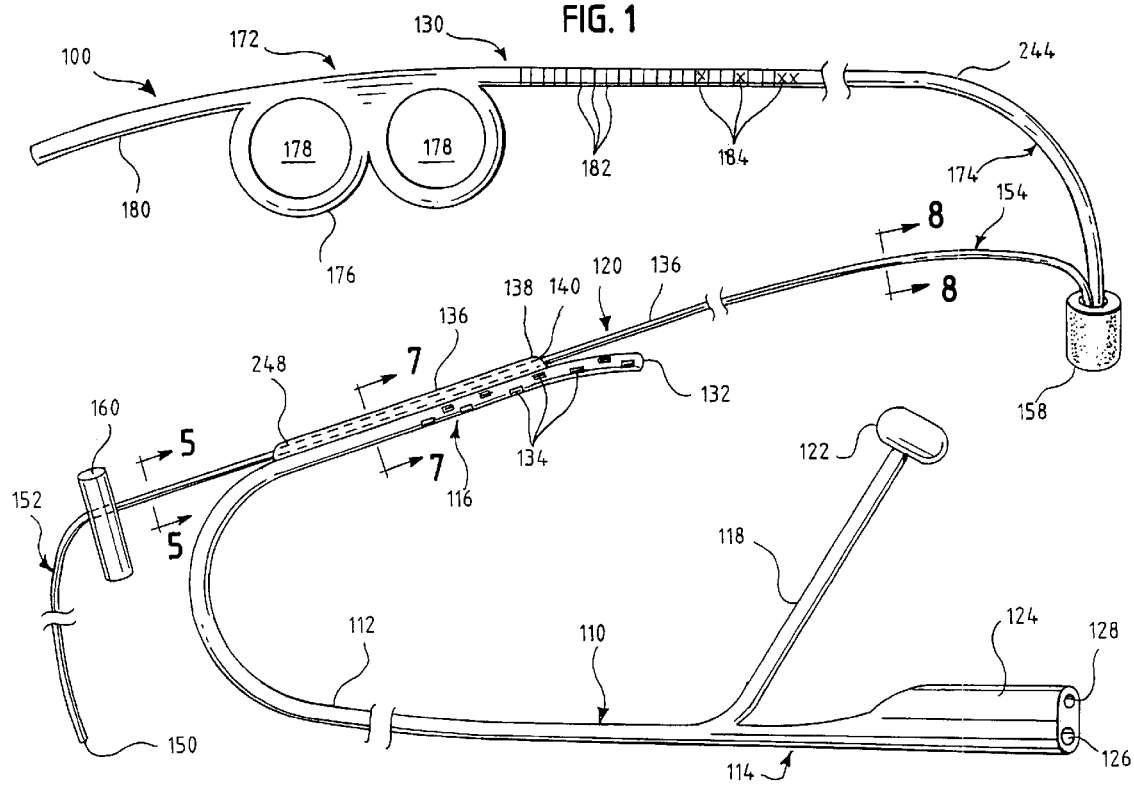
FIG. 1 is an overall side view of an exemplary embodiment of a nasogastric tube insertion system 100 constructed according to an aspect of the present invention.

As best seen in FIG. 1, the nasogastric tube insertion system 100 comprises a nasogastric tube 110, a guide element 120, and an inserter element 130. The function of the inserter element 130 is to aid in the initial placement of a portion of the guide element 120 in the patient's oropharynx. The function of the guide element 120 is to establish a desired path for passage of nasogastric tube 110 through the patient's nasal passages, the oropharynx, the esophagus, and the stomach, and to guide the nasogastric tube 110 along that path during the tube's insertion.

FIG. 1 depicts a configuration in which the nasogastric tube 110, guide element 120, and inserter element 130 are simultaneously connected to or engaged with one another, and a commercial embodiment of the nasogastric tube insertion system 100 could be so constructed. However, it will be appreciated that is not necessary that these components ever actually be arranged in that configuration. It is sufficient that the guide element 120 be attached to the inserter element 130 during the insertion of a portion of the guide element into the patient's oropharynx. In a subsequent step, it is sufficient that the guide element 120 be partially enveloped by or threaded through a portion of the nasogastric tube 110 during the insertion of the tube 110 in order that the tube 110 follow the path established by the guide element 120.

Figure 11:
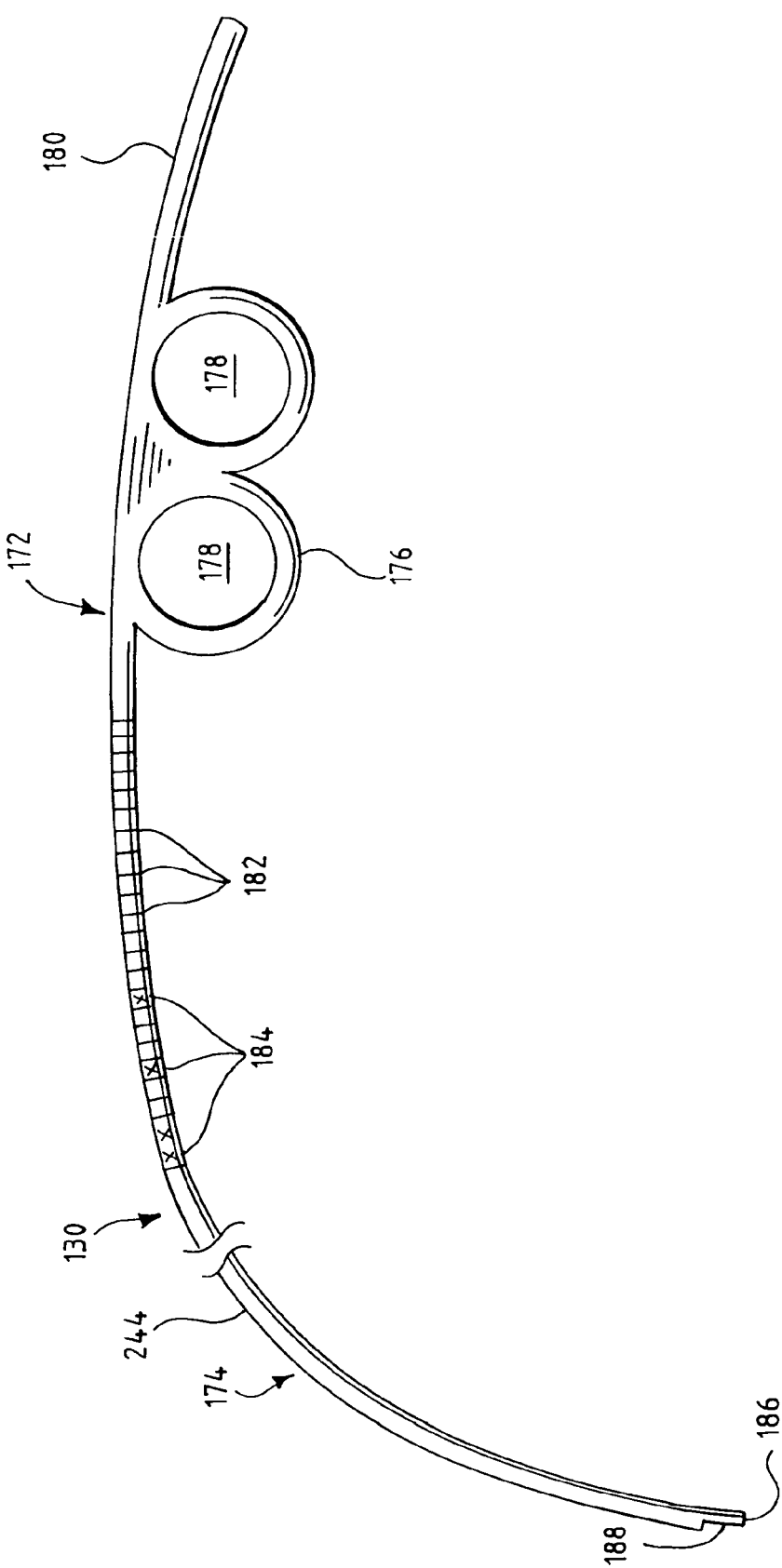
FIG. 11 is a side view of an inserter element 130 of the nasogastric tube insertion system 100 of FIG. 1.

As best seen in FIGS. 1 and 11, the inserter element 130 is constructed as a generally thin, longitudinal member having predominantly straight, slender, and elongate main body section 172 and a curved insertion section 174 which is adopted to engage an end of guide element 120 to enable insertion of the guide element into the patient's nasal passage or oropharynx. The insertion section 174 shown and described in connection with these figures is a first exemplary embodiment constructed according to an aspect of the present invention. An alternative embodiment 270 of the insertion section, adapted for use with an alternative embodiment 250 of the leading section of guide element 120, is shown in FIGS. 21-22 and described further in greater detail.

The inserter element 130 preferably comprises a handle 176 to allow the inserter element 130 to be readily grasped and controlled by a user. An exemplary configuration for handle 176 is shown in FIGS. 1 and 11, in which the handle is formed as two loops of structural material attached to and extending downward from the main body 172. The loops form handle openings 178, which may, for example, receive the user's index and middle fingers and allow the inserter element 130 to be grasped. A stabilizing extension 180 extending from the main body section rearward of the handle 176 improves stability during handling of the inserter element 130. Other handle configurations could also be used.

The main body 172 of the inserter element 130 may be constructed of any suitable material having sufficient thickness and strength to be handled and to support the modest weight of the insertion section 174 and a portion of the guide element 120 which is attached thereto during the insertion process. For example, the insertion section 174 may be constructed of semi-flexible, biologically inert material, such as clear poly-vinyl chloride. Other materials could also be used. The cross section and exact dimensions of the main body 172 are non-critical but may be selected to optimize cost, user comfort, and compatibility with the insertion section 174.

The insertion section 174 preferably has one or more curved portions such that it generally conforms to the anatomy of a typical patient's nasal passages and oropharynx. The curved portions may cumulatively provide curvature in the range of approximately 70 to 100 degrees of arc in the direction of the handle 176.

The insertion section 174 is preferably constructed of a flexible, biocompatible material, providing sufficient stiffness to support the swallowable weight 158 of guide element 120, but also providing enough flexibility to deform as needed, during insertion of the insertion section 174 into the patient's nasal passages, to pass any obstacles encountered without injury or abrasion. For example, the insertion section 174 may be constructed of semi-flexible, biologically inert material, such as clear poly-vinyl chloride. Other materials could also be used. The insertion section 174 may have any suitable cross section, including without limitation a generally circular, semi-circular, oval, oblong, or rectangular cross section. The cross-section of insertion section 174 may permit more flexibility in the direction of curvature than in directions perpendicular thereto. As discussed further in greater detail, the insertion section 174 preferably has a groove or channel 194 (FIG. 13) along at least a portion of its dorsal surface to receive a portion of the guide element 120. The insertion section 174 is preferably free of sharp exterior edges or other structures that may cause injury or abrasion of tissues in the nasal passages.

The exact dimensions of the insertion section 174 are non-critical, but preferably are selected as appropriate for the material used, to provide a desired amount of stiffness and flexibility, and to allow the inserter to easily enter and pass through the nasal passages of a patient. The insertion section 174 should be long enough that, when inserted, the tip 186 can reach into the patient's oropharynx without requiring the handle 176 to impinge on the patient's face. It is believed that an insertion section 174 having a width less than or equal to about 0.75 cm, a thickness less than or equal to about 0.5 cm, and a length of approximately 25 cm or more, would be appropriate for use with an adult patient of typical size. Smaller dimensions may be needed for use with smaller patients, including children and infants. In addition, the dimensions could be varied to achieve desired variations in stiffness or other mechanical parameters. For example, if increased flexibility is desired toward the end of the insertion section 174, the thickness or width may be gradually reduced in that section. The main body 172 and insertion section 174 may be separately constructed and later assembled to form a unit. Alternately, the main body 172 and insertion section 174 may be constructed as a single unit, and there may be no visible structural characteristics that signal when one ends and the other begins.

The inserter element 130 preferably has measurement lines 182 or other suitable indicia to allow the user to readily ascertain when the inserter has been inserted to a predetermined insertion depth, corresponding to the placement of the end of the insertion section 174, and the swallowable weight 158 attached thereto, in a desirable location in the patient's oropharynx. For most patients, an optimal predetermined insertion depth may be found by measuring the distance between the patient's earlobe and the tip of the patient's nose. The inserter element 130 may also have measurement legend indicia 184 specifying units of measurement or other related information associated with measurement lines 182. However, the user may perform the distance measurement using the inserter element 130 itself, e.g., by marking the distance on the measurement lines 182.

Although it is normally expected that the desired inserter-assisted placement of the swallowable weight 158 be into the patient's oropharynx, it may be preferable in some situations to use the inserter element 130 to place the swallowable weight 158 only part way into the nasal passages. In those situations, the swallowable weight 158 would then be released from the inserter element 130, and the user would advance the guide element 120 into the oropharynx by applying longitudinal pressure, relying on the stiffness of the guide element to assist placement. A shorter inserter element 130 could be used for such situations, and the desired insertion distance could be measured using different benchmarks on the patient's face or body.

As best seen in FIG. 13, the insertion section 174 preferably has a walls 196 forming a groove or channel 194 along at least a portion of its dorsal surface 244 to receive the guide element 120. An alternative embodiment 270 of the insertion section is shown in FIGS. 21-23 and described further in greater detail. Once the swallowable weight 158 of the guide element 120 is placed on the end of the inserter element 130, in order to retain the swallowable weight 158 in position, the user must apply light tension on the guide element 120. The channel 194 is adapted to retain the guide element 120 along the top surface of the inserter element 130 while tension is applied. This avoids undesirably deforming the insertion section 174 and prevents the guide element 120 from taking on a "bow string" configuration, which would interfere with the insertion process.

Although channel 194 is depicted in FIG. 13 as a generally U-shaped channel of considerable depth, other configurations could also be used provided they retain the guide element 120 along the dorsal surface 244 of the inserter element 130 while light tension is applied to the guide element 120. For example, the depth of the channel could be significantly less than depicted. For another example, the channel-forming walls 196 could be formed as two or more longitudinal ridges on the dorsal surface of the guide element 120, which might otherwise be flat. The ridges could be of any height that satisfactorily retains the guide element 120 while light tension is applied. The term "dorsal" is used here to refer to the upper surface 244 of the inserter element 130, as shown in FIGS. 1 and 11, without respect to the orientation in which the inserter element 130 is held.

As best seen in FIGS. 11-13, the tip 186 of the insertion section 174 has a stepped engagement section 188 of reduced thickness for loosely engaging the swallowable weight 158 of the guide element 120. As mentioned above, once the swallowable weight 158 is placed onto the tip 186 of the insertion section 174, the tip is preferably held in place by light tension on guide element 120. The loose engagement preferably allows the swallowable weight 158 to be released from the tip 186 by releasing tension on the guide element 120, allowing the swallowable weight 158 to fall away. FIGS. 12 and 13 depict the tip 186 and stepped engagement section 188 in alternate configurations. FIGS. 21 and 23 depict an alternative embodiment 270 of the insertion section and will be discussed further in greater detail.

In FIG. 12, there is shown a first embodiment in which the tip 186 has an angular chamfered section 190 adapted to engage a mating receptacle 168 of the swallowable weight 158 of the guide element 120. Substantially vertical step walls mark the boundary between the full-thickness portion of the insertion section 174 and the stepped engagement section 188. The stepped engagement section 188 extends a short distance from the step walls 198 to the tip 186. The leading section 154 of guide element 120 is retained in channel 194 (FIG. 13) when the swallowable weight 158 is placed on tip 186 and light tension is applied to guide element 120.

In FIG. 13, there is shown a second embodiment in which the tip 186 has a substantially vertical wall section 192 instead of the angular chamfered section 190 of FIG. 12. Angular step walls 242 mark the boundary between the full-thickness portion of the insertion section 174 and the stepped engagement section 188. The stepped engagement section 188 extends a short distance from the step walls 242 to the tip 186. The leading section 154 (FIG. 12) of guide element 120 is retained in channel 194 when light tension is applied to guide element 120.

Figure 2:
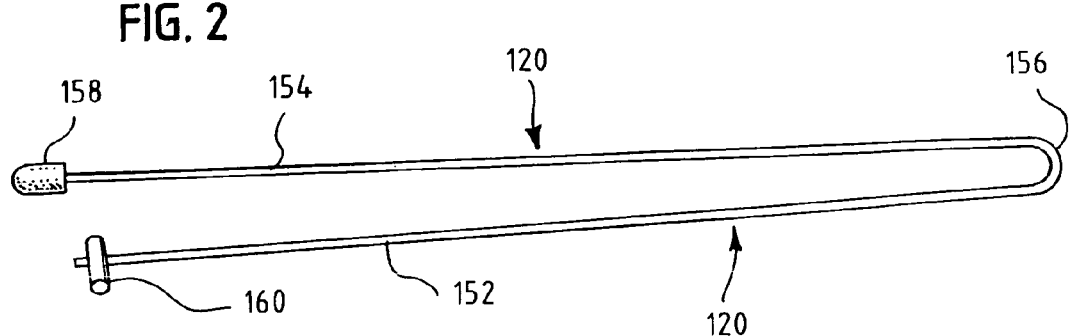
FIG. 2 is a side view of a guide element 120 of the nasogastric tube insertion system 100 of FIG. 1, showing the guide element in another configuration.

As best seen in FIGS. 1-2, the guide element 120 is constructed as a thin, elongate or generally longitudinal element, which may be a cord or line, having a leading section 154 having sufficient flexibility to be easily inserted into and swallowed by the patient, and trailing section 152 having sufficient rigidity to guide the nasogastric tube 110 as the tube is inserted. The trailing section also functions as a tether. A swallowable weight 158 is attached to the leading section 154. A transition 156 joins the trailing section 152 and leading section 154. A stopper 160 may be provided near the end 150 of guide element 120 opposite the swallowable weight 158 to prevent the end from being swallowed by the patient. Alternatively, the trailing section 152 could be extremely long, such that it cannot be swallowed. An alternative embodiment 250 of the leading section of guide element 120 is shown in FIGS. 21-22 and described further in greater detail.

The trailing section 152 of the guide element 120 may be constructed of any suitable material having sufficient thickness, flexibility and strength to be handled and to reliably avoid breakage. The trailing section 152 is preferably be rigid enough to navigate over the trachea and into the esophagus, but flexible enough to be readily swallowed. For example, the trailing section 152 may be constructed of a silicone elastomer or of a polymer in the nylon family. Other highly-flexible, biologically inert materials could also be used.

The leading section 154 is preferably constructed of any suitable biocompatible material, having sufficient thickness, flexibility and strength to be handled and to reliably avoid breakage. The leading section 154 is preferably flexible enough to be very easily swallowed. Because the leading section 154 will be swallowed and will be subject to digestive acids and enzymes for some period, the material from which the leading section 154 is constructed is preferably highly resistant to attack from such agents. For example, the leading section 154 may be constructed of a silicone elastomer or of a polymer in the nylon family. Other highly-flexible, biologically inert materials could also be used. Preferably, the trailing section 152 is free of sharp edges and has suitable outer surface features and finish to avoid injury or abrasion of tissues when the leading section 154 is swallowed and removed. In some situations, it may be desirable to use the inserter element 130 to assist the insertion of the leading section 154 of guide element 120 only part way into the patient's nasal passages, and then to use longitudinal pressure on the guide element 120 to further advance the leading section 154 into the patient's oropharynx without the continued assistance of the inserter element 130. In such situations, it is desirable that leading section 154 possess sufficient stiffness accommodate advancement of the leading section into the oropharynx, while retaining sufficient flexibility to avoid damaging tissues during insertion and removal.

Figure 5:
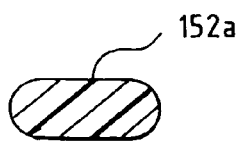
FIG. 5 is a cross-section view of the trailing section 152 of the guide element 120 of FIG. 1 taken along section line 5-5 thereof.
Figure 6:
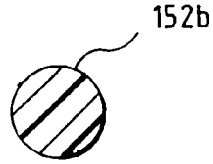
FIG. 6 is a cross-section view of an alternate embodiment of the trailing section 152 of the guide element 120 of FIG. 1 taken along section line 5-5 thereof.
Figure 7:
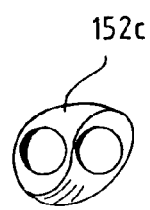
FIG. 7 is a cross-section view of another alternate embodiment of the trailing section 152 of the guide element 120 of FIG. 1 taken along section line 5-5 thereof.
Figure 8:
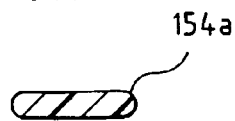
FIG. 8 is a cross-section view of the leading section 154 of the guide element 120 of FIG. 1 taken along section line 8-8 thereof.
Figure 9:
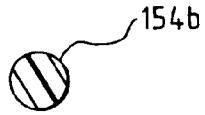
FIG. 9 is a cross-section view of an alternate embodiment of the leading section 154 of the guide element 120 of FIG. 1 taken along section line 8-8 thereof.

As best seen in FIGS. 5-7 and 8-9, the longitudinal elements 152, 154 of the guide element 120 may be constructed as a unitary or monofilament line or piece, or as a string or cord, or similar form of stranded or woven multifilament line. FIGS. 5 and new 08 depict in cross section a first exemplary embodiment of the guide element 120 in which the trailing section 152a is formed as an element of generally oval or oblong cross section, and the leading section 154a is also formed as an element of generally oval or oblong cross section of somewhat reduced size. FIGS. 6 and 9 depict in cross section a second exemplary embodiment of the guide element 120 in which the trailing section 152b is formed as an element of generally circular cross section, and the leading section 154b is also formed as an element of generally circular cross section of somewhat reduced size. FIG. 7 depicts in cross section a third exemplary embodiment of the guide element 120 in which both the trailing and leading section 152c are formed as a twisted bifilar cord. The elements may be formed by molding, extrusion, drawing, or any other suitable method of manufacture. These particular configurations are provided by way of example, not limitation, and it will be appreciated that other cross sections, number of filaments, stranding configurations, and the like could also be used, and that the configuration used for the leading section 154 may differ from that used for the trailing section 152.

The exact dimensions of the leading section 154 and the trailing section 152 of guide element 120 are non-critical but may be selected to optimize cost, compatibility with one another, and with a guide element retaining structure 136 of nasogastric tube 110 (FIGS. 1, 10), discussed further in greater detail. A leading section 154 having a width in the range of approximately 0.1-2.5 mm and a thickness in the range of approximately 0.1-2.5 mm, would be appropriate, but the necessary dimensions may vary depending on material choices, the flexibility or stiffness desired, and other factors. A trailing section 152 having a width in the range of approximately 0.1-3.5 mm, and a thickness in the range of approximately 0.1-3.5 mm would be appropriate, but the necessary dimensions may vary depending on material choices, the flexibility or stiffness desired, and other factors. The trailing section 152 and leading section 154 may be separately constructed and later assembled to form a unit. Alternately, the trailing section 152 and leading section 154 may be constructed as a single unit. A transition area 156 designates the area at which trailing section 152 is joined to leading section 154. If these components are formed as an integrated unit of the same size and cross-section throughout, the transition area may not be apparent. If the trailing section 152 and leading section 154 are dissimilar, the leading section 154 is preferably long enough to allow the patient to swallow the swallowable weight 158 into the stomach without ingesting part of the trailing section 152. Also, the change from leading section 154 to the trailing section 152 may be gradual rather than abrupt.

Figure 3:
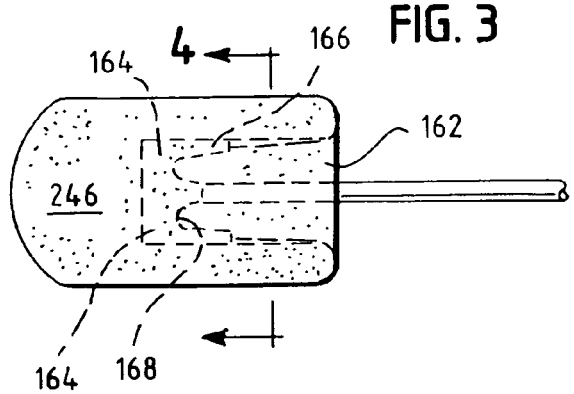
FIG. 3 is an enlarged side view of the leading section 154 of the guide element 120 of FIGS. 1-2.
Figure 4:
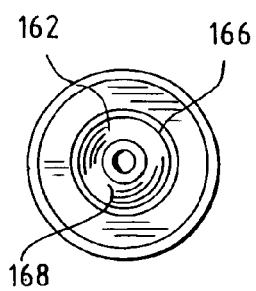
FIG. 4 is a partial cross-section view of the leading section 154 of the guide element 120 of FIGS. 1-3 taken along section line 4-4 of FIG. 3.

As best seen in FIGS. 3, 4, and 12, the swallowable weight 158 is attached to the leading section 154 of guide element 120. The swallowable weight 158 preferably comprises a resilient body 246 and an interior attachment structure 164 for affixing the shell to the leading section 154 of the guide element 120. An alternative embodiment 252 of the swallowable weight is shown in FIGS. 21 and 22, and described further in greater detail.

The body 246 is preferably soft and resilient so that it may be easily swallowed with minimal discomfort to the patient and so that it avoids abrading or irritating tissues when it is inserted through the patient's nasal passages into the oropharynx. The body 246 is preferably constructed from a flexible, absorbent, biocompatible material, which may, for example, be an spongiform material such as open-cell foam. Other materials could also be used. Because the body 246 will be swallowed and will be subject to digestive acids and enzymes for some period, the material from which the body 246 is constructed is preferably highly resistant to attack from such agents. Although the swallowable weight 158 is referred to as a weight, it need not be heavy or constructed of dense materials. It is sufficient that the weight be easily swallowed. The dimensions of the swallowable weight 158 are not critical, but the weight is preferably of a size that can be easily swallowed and can easily pass through the patient's nasal passages. A diameter in the range of approximately 0.4-1.25 cm, and a length in the range of approximately 0.7-1.7 cm is believed to be suitable for most adult patients. Other sizes could also be used; a smaller weight may be required for smaller patients, such as children and infants.

The interior attachment structure 164 may be any suitable structure that can be securely affixed to the body 246. For example, the attachment structure 164 may be formed as a cup-like element having a cylindrical attachment wall 166. However, other structures could also be used. The attachment structure 164 may be secured to the body 246 using any suitable fastening technology, including but not limited to glue, ultrasonic or chemical bonding or welding, structural features such as barbs or hooks, or a tight friction fit.

The leading section 154 of guide element 120 extends outward from the attachment structure 164 through an opening 162 in the body 246. The leading section 154 may be secured to the attachment structure 164 using any suitable fastening technology, including but not limited to glue, ultrasonic or chemical bonding or welding, or interlocking structural features. Alternatively, the attachment structure 164 may be formed as an integrated part of the leading section 154. As best seen in FIG. 3, the bottom 168 of the attachment structure 164, the attachment wall 166, and the leading section 154 form an evacuated-toroid-shaped space to receive the tip 186 of the insertion section 174 of the inserter element 130. This configuration enables the tip 186 to be held against the attachment structure 164 without piercing the resilient material of the body 246, which would undesirably produce a frictional engagement of these components. A loose engagement between swallowable weight 158 and tip 186 of leading section 154 of inserter element 130 is desirable to allow the swallowable weight 158 to be released from the tip 186 by releasing tension on the guide element 120, causing the swallowable weight 158 to fall away.

Figure 10:
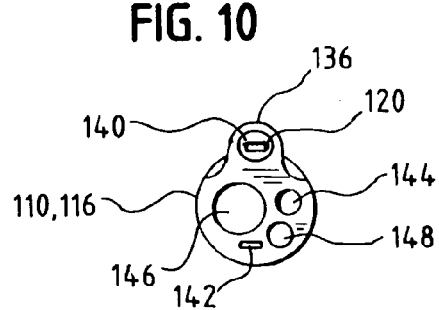
FIG. 10 is a cross-section view of a nasogastric tube 110 of the nasogastric tube insertion system 100 of FIG. 1, taken along section line 10-10 thereof.
Figure 18:
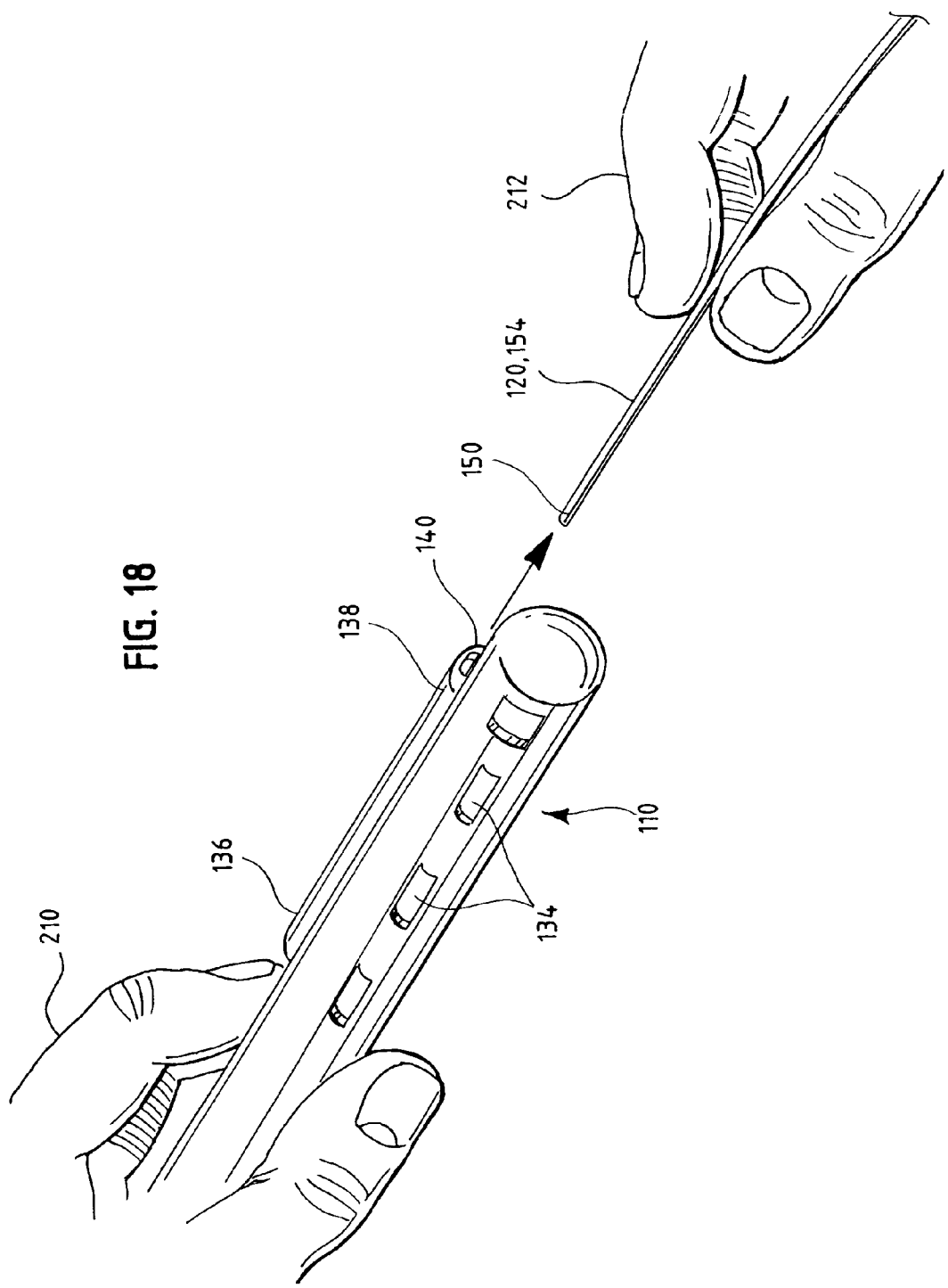
FIG. 18 is a side view showing the nasogastric tube 110 and the guide element 120, depicting another stage in the method of inserting the nasogastric tube insertion system 100, in which the guide element 120 is threaded through an opening of the guide element retaining structure 136 of the nasogastric tube 110.

As best seen in FIGS. 1 and 18, the nasogastric tube 110 is preferably constructed as a generally tubular structure comprising a main tubular section 112, a proximal end section 114, and a distal end section 116. The distal end section 116 is intended to be inserted into the patient. The proximal end section 114 is intended to remain outside of the patient. The nasogastric tube 110 includes one or more interior bores or lumina extending approximately the length of the tube 110. As best seen in FIG. 10, an exemplary embodiment of nasogastric tube 110 has three interior bores or lumina 144, 146, and 148, but more or fewer lumina could be used depending on the application and the permissible thickness of the nasogastric tube 110. For example, nasogastric tube 110 may have a single lumen for use as a feeding tube to allow the direct introduction of food or nutritional supplements into the patient's stomach. Nasogastric tube 110 may also comprise a radiopaque tracer strip 142 to allow the position of the nasogastric tube 110 to be verified using radiographic or fluoroscopic examination.

The proximal end section 114 may separate into two or more breakout segments, each including one or more of the lumina 144, 146, 148. As best seen in FIG. 1, in an exemplary embodiment, proximal end section 114 separates into a first breakout tube 118, carrying lumen 144, and a second breakout tube 124 carrying lumina 146 and 148. Second breakout tube 124 provides openings 126 and 128 into lumina 146 and 148 to allow connection of the lumina to a source of fluid to be introduced into the stomach, or a vacuum "supply to remove fluid from the stomach, or to allow the lumen to be vented to the atmosphere. First breakout tube 118 has an opening (not shown) into first lumen 144. As best seen in FIG. 1, a one-way valve 122 may be connected to one of the lumina to control ventilation of the stomach.

The distal end section 116 has a leading end 132. Adjacent the leading end 132, there is provided a plurality of openings 134 leading to the interior bores or lumina 144, 146, and 148 and allowing fluid and gas communication between the lumina 144, 146, and 148 and the exterior space surrounding the leading end 132. The opening or openings leading to a particular one of the lumina may be spaced from the openings leading to other lumina as required by the application. For example, if one lumen is assigned to introduce fluids into the stomach, and another lumen is assigned to remove fluids from the stomach, it may be desirable to separate the corresponding openings so that the fluids newly introduced are not immediately removed.

The distal end section 116 of nasogastric tube 110 further comprises a guide element retaining structure 136 adapted to move slidably along guide element 120. As best seen in FIGS. 1 and 10, the guide element retaining structure preferably comprises a generally tubular protrusion or intrusion attached and parallel to proximal end section 114 having a tubular opening 140 to receive the guide element 120. Once the guide element has been inserted, the guide element retaining structure 136 allows the nasogastric tube 110 to move slidably and telescopically along the guide element 120. Thus, the guide element 120 may serve to establish a path for the nasogastric tube 110 to follow as it is inserted through the patient's nasal passages, oropharynx, esophagus, and into the patient's stomach. The leading end 138, and a trailing end 248 of the guide element retaining structure 136 are preferably chamfered to avoid abrading or irritating tissues which are encountered as the nasogastric tube 110 is inserted and removed.

Although the guide element retaining structure 136 is shown in FIGS. 1 and 10, and described herein as a tubular element attached to the distal end section 116, other structures could also be used to form the guide element retaining structure 136 adopted for slidable and/or telescopic movement along the guide element 120. For example, the guide element retaining structure 136 could be formed as one or more loops or retaining tabs attached to the distal end section 116. For another example, the guide element retaining structure 136 could be formed as a tunnel-style bore through an unused portion of the cross section of the nasogastric tube 110. This configuration has the advantage that no enlargement of the cross-sectional size of the nasogastric tube 110 is needed, but it may not be possible to implement if the tube is crowded. As a further alternative to a separate structure 136 dedicated to retaining the guide element 120, features of the distal end 116 of the nasogastric tube 110 may be used to form a guide element retaining structure. For example, guide element 120 could be threaded or telescoped through an aperture placed at or adjacent the tip 132 of the distal end section 116 of the nasogastric tube 110, extend through one of lumina 144, 146, or 148, and could exit through one of the openings or apertures 134 in communication with such lumen and spaced from the tip 132.

The dimensions of the nasogastric tube 110 are non-critical, but must be selected to allow the tube to be inserted through the nasal passages and into the stomach, and to remain there without interfering with the patient's respiration. A smaller diameter, if permitted by the requirements for the lumina inside the tube, is generally preferable in that it minimizes patient discomfort. A nasogastric tube 110 having a diameter of approximately 0.25 inches is believed to be suitable for most adult patients. The length of the nasogastric tube 110 should be long enough to extend into the patient's stomach, with some additional length outside the patient to allow for convenient external connections and to prevent the patient from inadvertently swallowing the proximal end section 114 of the nasogastric tube 110.

The nasogastric tube 110 is preferably constructed of any suitable biocompatible material, having sufficient thickness, flexibility and strength. Because the nasogastric tube 110 will be swallowed and will be subject to digestive acids and enzymes for some period, the material from which the nasogastric tube 110 is constructed is preferably non-porous and highly resistant to attack from such agents. For example, the nasogastric tube 110 may be constructed of a silicone elastomer. Other flexible, biologically inert materials could also be used. The nasogastric tube 110 is preferably transparent or translucent to allow visual inspection of the lumina for proper operation.

FIGS. 14-19 depict several steps in a exemplary methods 310, 310a (FIG. 20) according to an aspect of the present invention for use in conjunction with the nasogastric tube insertion system 100 of FIGS. 1-13.

Figure 20:
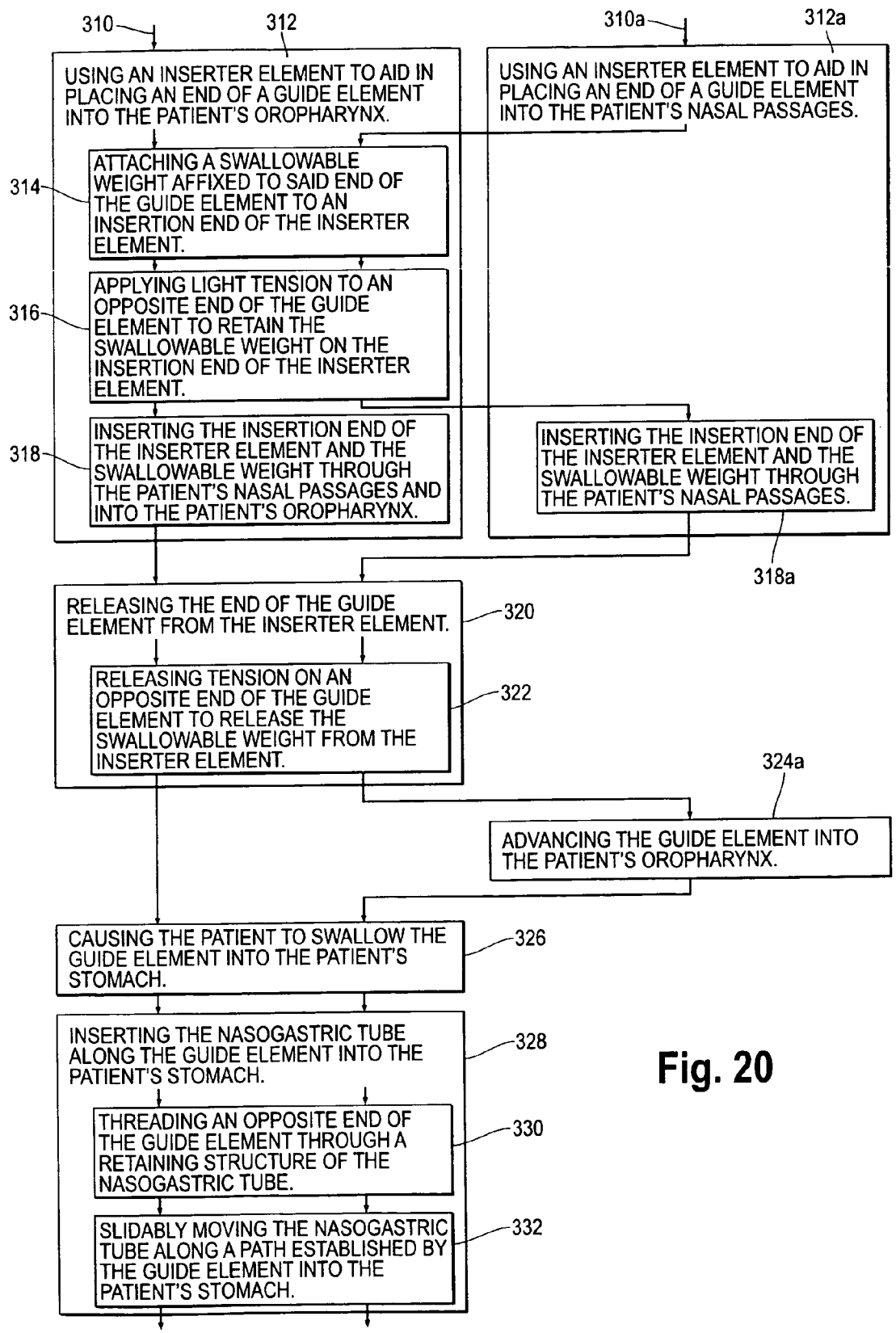
FIG. 20 is a flow diagram depicting steps of exemplary methods 310, 310a of inserting the nasogastric tube insertion system 100 into the patient.

FIG. 20 is a flow diagram depicting steps of exemplary methods 310, 310a. In method 310, the inserter element 130, with the swallowable weight 158 engaged to the insertion end thereof, is used to insert the swallowable weight through the patient's nasal passages and into the oropharynx. In method 310a, the inserter element 130 is used to insert the swallowable weight through the patient's nasal passages. Then the swallowable weight 158 is released from the end of inserter element 130 and is advanced into the patent's oropharynx, by, for example, gentle longitudinal pressure on the guide element 120 in the direction of the patient's oropharynx.

In other respects, the methods 310 and 310a are similar. The term "step" is used herein to refer to both the general steps associated with one of methods 310, 310a, and to more detailed substeps which may be comprised as part of a more general step. Some steps are optional.

A first group of steps 312, 314, 316 is generally depicted in FIG. 14. The user grasps the handle 176 (FIGS. 1 and 11) of inserter element 130 using a first hand 212. The user places the swallowable weight 158 on the tip 186 of insertion section 174 of inserter element 130 (step 314). The user then uses a second hand 210 to apply light tension on guide element 120, thereby maintaining the swallowable weight 158 in position on the end of inserter element 130 (step 316)

Figure 15:
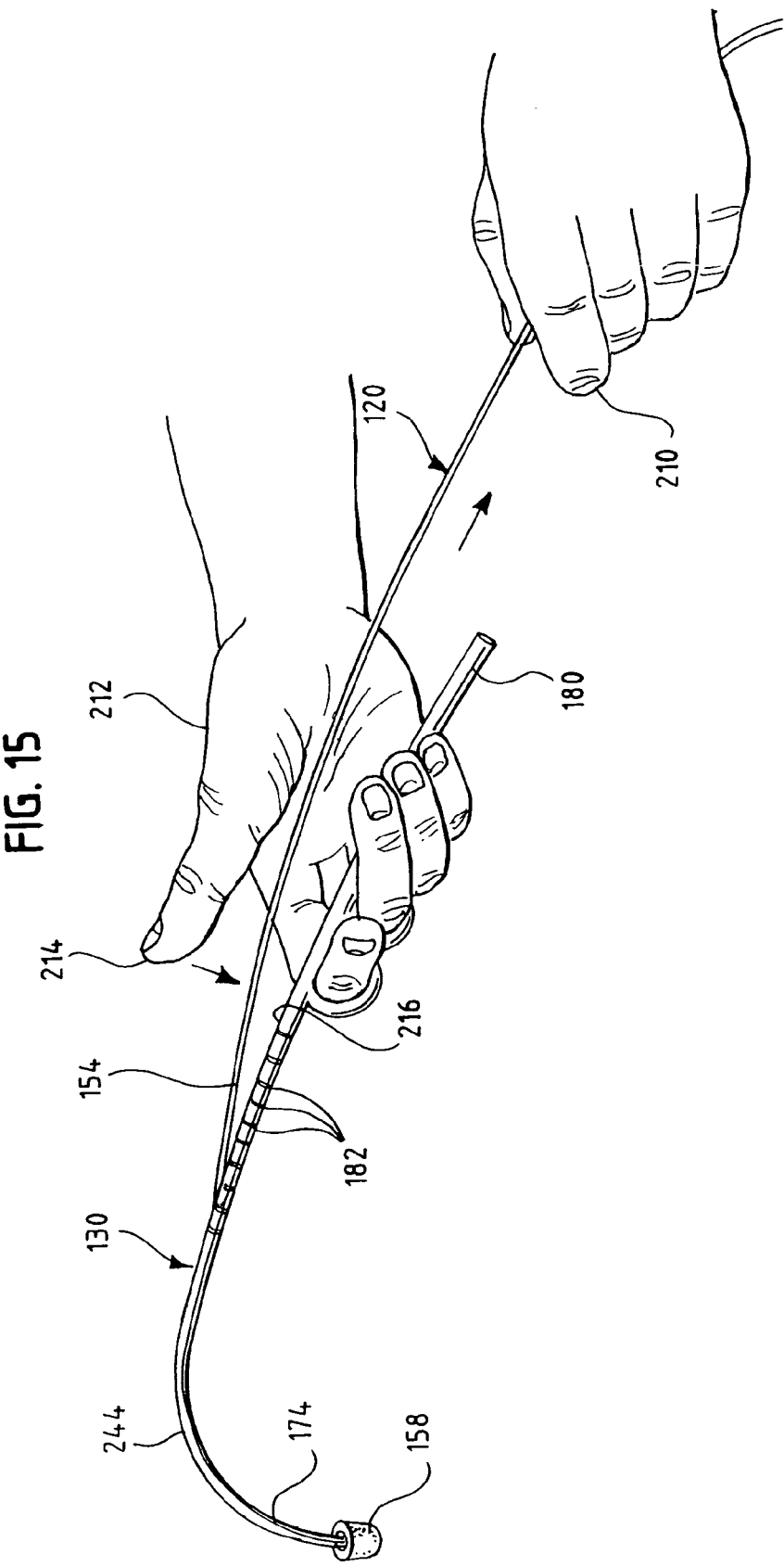
FIG. 15 is a side view showing the guide element 120 of FIGS. 1-4 attached to the inserter element 130 of FIGS. 1, 11, and 12, and depicting another stage in the method of inserting the nasogastric tube insertion system 100 in which the swallowable weight 158 is held on the tip 186 of inserter element 130 by tension on the guide element 120 provided by the user.

A second group of steps is generally depicted in FIG. 15. The user uses the second hand 210 to gently pull the guide element 120 rearward, in order to position the guide element 120 in channel 194 (FIG. 13) on the dorsal surface of inserter element 130. The user must allow controlled slippage of the guide element 120 to allow the second hand to move rearward while maintaining light tension on guide element 120. The user then uses the thumb 214 of the first hand to trap the guide element 120 under light tension against the dorsal surface of the inserter element 130. This prevents the swallowable weight 158 from falling off of the inserter element 130.

In an optional step, the user may transfer the inserter element 130 and guide element 120 from the first hand to the second hand. Subsequent steps assume this has been done.

In another optional step, the user may apply one or more of an anesthetic (such as lidocaine), and a vasoconstrictor (such as epinephrine), to the absorbent material of the swallowable weight 158. The anesthetic numbs the passage to the stomach. The vasoconstrictor causes vasoconstriction of the nasal mucosa allowing for easier passage and decreased bleeding. This step may be performed, for example, by dipping the swallowable weight 158 into a container of these substances. The anesthetic and vasoconstrictor agents may be packaged with the nasogastric tube insertion system 100, to promote their use. Also, the swallowable weight 158 may be pre-moistened with the anesthetic and vasoconstrictor agents by a manufacturer or distributor, to relieve the user of the burden of applying the agents, and to minimize the risk of contamination which might occur in bulk containers of the agents in a clinical environment.

Figure 16:
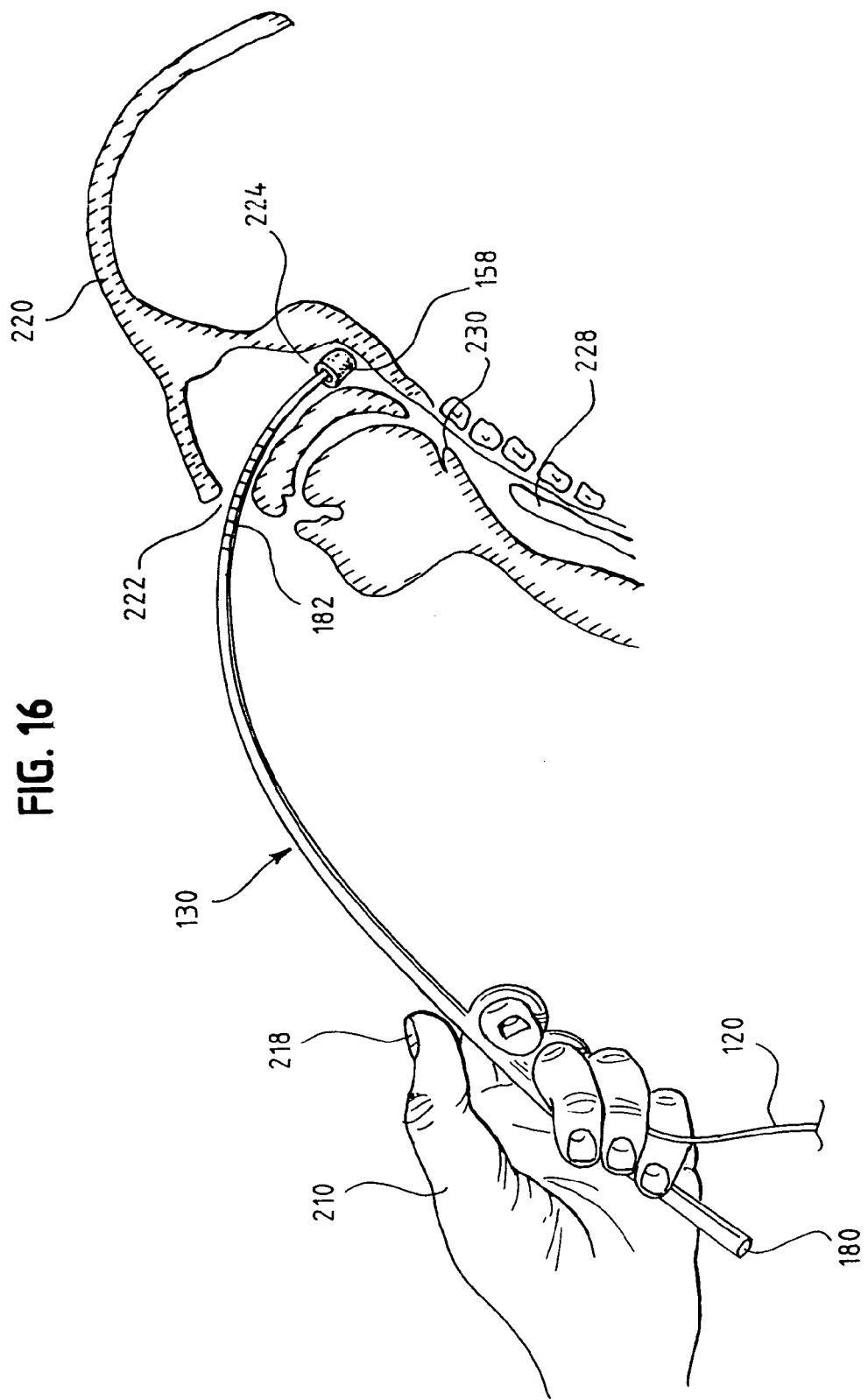
FIG. 16 is a side view and stylized partial cross-section view showing the inserter element 130 and guide element 120, depicting another stage in the method of inserting the nasogastric tube insertion system 100, in which the inserter element 130 and guide element 120 are being inserted through the patient's nasal passages to the oropharynx.

A third group of steps 318 is generally depicted in FIG. 16. The user inserts the inserter element 130 and guide element 120 through the patient's nostril 222, through the nasal passages, and into the oropharynx 224 (step 318). The user maintains pressure on guide element 120 using the thumb 218 during this process to keep the swallowable weight 158 in position. The user is preferably guided by measurement indicia 182 to insert the inserter element 130 to a predetermined insertion depth measured earlier. For most patients, an optimal predetermined insertion depth may be found by measuring the distance between the patient's earlobe and the tip of the patient's nose.

Figure 17:
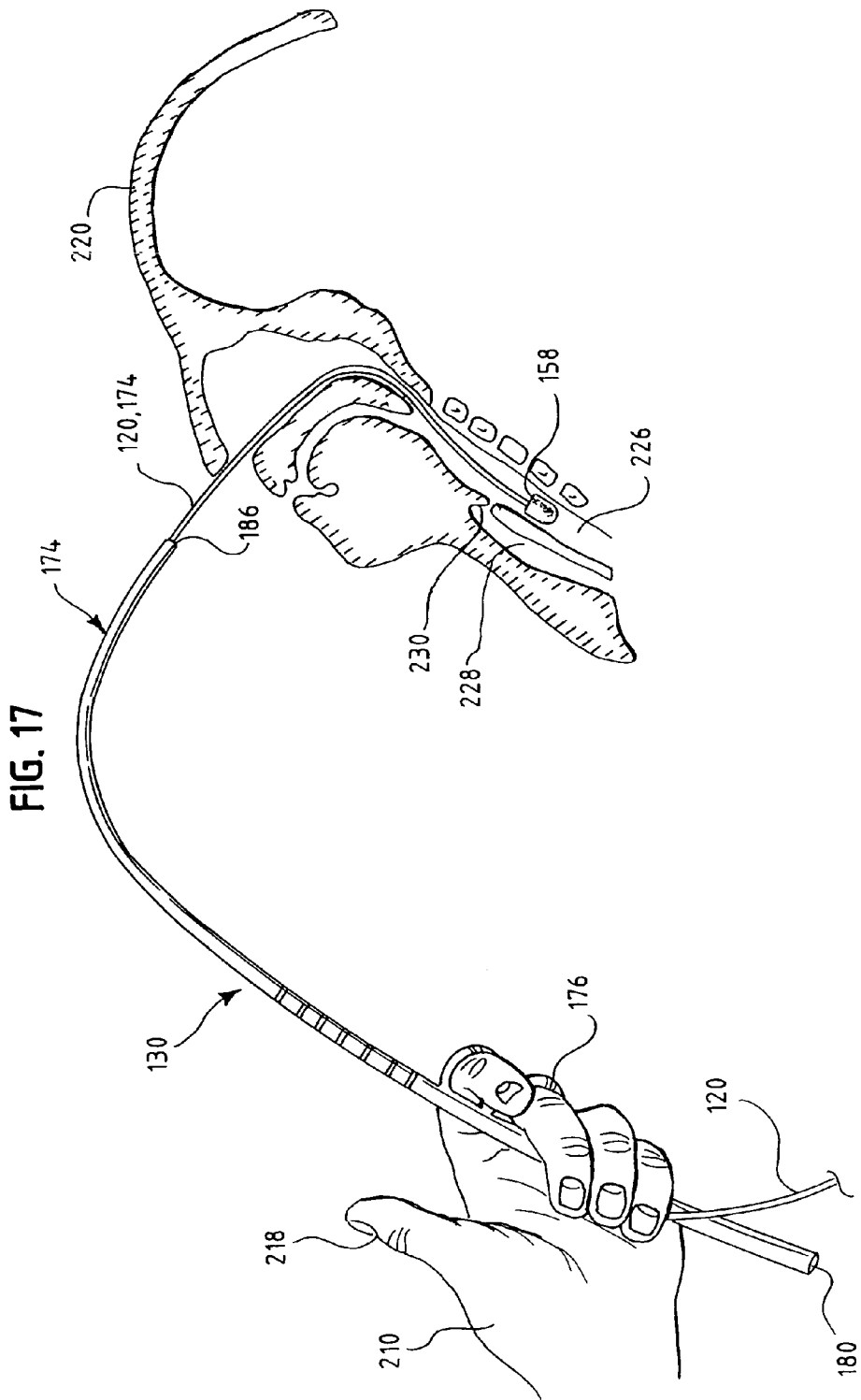
FIG. 17 is a side perspective view and stylized partial cross-section view showing the inserter element 130 and guide element 120, depicting another stage in the method of inserting the nasogastric tube insertion system 100, in which the inserter element 130 is removed and the swallowable weight 158 of the guide element 120 is being swallowed past the epiglottis.

A fourth group of steps 320, 322, 326 is generally depicted in FIG. 17. The user releases thumb 218, thereby relieving pressure on the guide element 120, and freeing the swallowable weight 158, allowing it to fall (steps 320, 322). At approximately the same time, the patient is instructed to swallow the swallowable weight 158 (step 326). The patient may be given some water to sip to assist in swallowing. As a consequence of swallowing, the patient's epiglottis 230 covers the trachea 228, ensuring that the swallowable weight 158 is carried into the esophagus 226, and then into the stomach. The trailing section 152 and proximal end 150 of guide element 120 remains outside the patient. The user then removes the inserter element 130, which is no longer required for this procedure.

Although the steps heretofore described in connection with FIGS. 16-17 contemplate that the inserter 130 be used to place the swallowable weight 158 all the way into the patient's oropharynx 222, it may be preferable in some situations to use the inserter element 130 to place the swallowable weight 158 only part way into the nasal passages—that is, between the nostril 220 and the oropharynx 222. In an alternative submethod 310a according to an aspect of the present invention for use in conjunction with the nasogastric tube insertion system 100 of FIGS. 1-13, the steps of FIGS. 16-17 may be modified as follows: The user inserts the inserter element 130 and guide element 120 through the patient's nostril 222, and into a predetermined location in the nasal passages, but not as far as the oropharynx 224 (step 312a-318a). The user maintains pressure on guide element 120 using the thumb 218 during this process to keep the swallowable weight 158 in position (step 316). The user is preferably guided by measurement indicia 182 to insert the inserter element 130 to a predetermined insertion depth measured earlier. For most patients, an optimal predetermined insertion depth may be found by measuring the distance between selected benchmarks on the patient's face or body. A shorter inserter element 130 may be used. The user releases thumb 218, thereby relieving pressure on the guide element 120, and freeing the swallowable weight 158 (steps 320, 322). The inserter element 130 may optionally be retracted, or it may be temporarily left in place to support the guide element 120 during advancement of the swallowable weight into the oropharynx.

The user applies gentle longitudinal pressure to guide element 120 to further advance the swallowable weight 158 into the oropharynx 222, noting by feel or by patient reaction when the weight has arrived in the desired position (step 324a). The patient is then instructed to swallow the swallowable weight 158 (step 326). The patient may be given some water to sip to assist in swallowing. As a consequence of swallowing, the patient's epiglottis 230 covers the trachea 228, ensuring that the swallowable weight 158 is carried into the esophagus 226, and then into the stomach. The trailing section 152 and proximal end 150 of guide element 120 remains outside the patient. The user then removes the inserter element 130, if present. The remaining steps of methods 310 and 310a are similar.

A fifth group of steps 328, 330 is generally depicted in FIG. 18. The user threads the proximal end 150 of the guide element 120 through the retaining section opening 140 of the guide element retaining structure 136 of nasogastric tube 110 (step 330). This step is optional; the nasogastric tube 110 may be supplied by the manufacturer, or otherwise distributed to the user, in the condition in which the guide element 120 is already telescoped through the guide element retaining structure 136.

Figure 19:
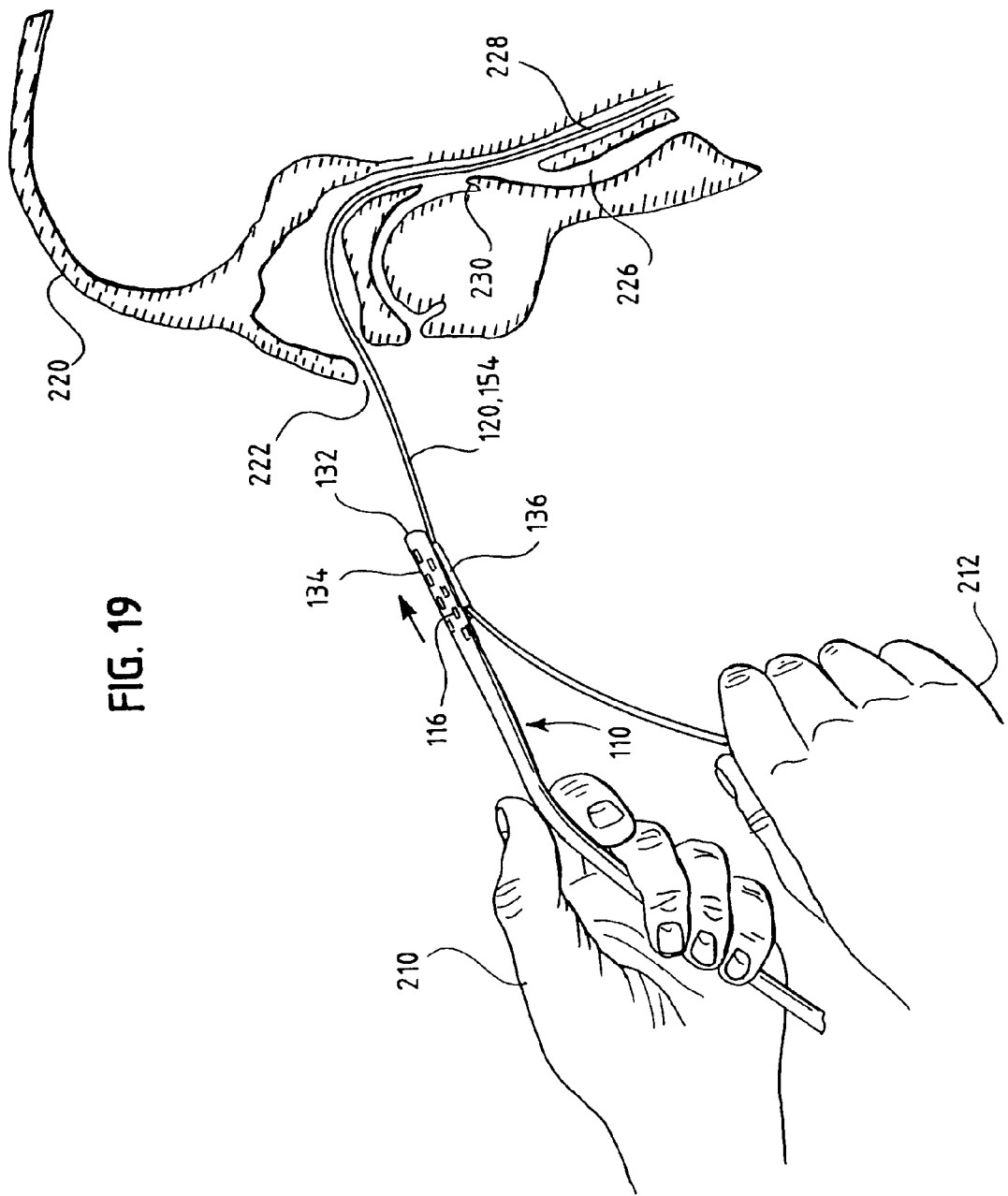
FIG. 19 is a side view and stylized partial cross-section view showing the nasogastric tube 110 and the guide element 120, depicting another stage in the method of inserting the nasogastric tube insertion system 100, in which the nasogastric tube 110 is pushed along the guide element 120 as the tube is inserted into the patient's nasal passage.

A sixth group of steps 328, 332 is generally depicted in FIG. 19. Holding the guide element 120 firmly in a first hand 212, and the nasogastric tube 110 in a second hand 210, the user pushes the nasogastric tube 110 telescopically along the guide element 120. The user inserts the nasogastric tube 110 through the nostril 222 and the tube safely follows the path established by the guide element 120 into the patient's stomach (step 332). The guide element 120 and nasogastric tube 110 remain together until the nasogastric tube 110 is to be removed. Then, the nasogastric tube 110 and the guide element 120 are removed together.

Although the shape of the swallowable weight 158 has been shown in FIG. 1 and as generally cylindrical, there may be situations in which a different shape is advantageous. Especially upon removal of the nasogastric tube 110 and guide element 120, a gentler transition from the thin leading section 154 of the guide element to the full diameter of the swallowable weight 158 may ease passage of the swallowable weight through the patient's esophagus, nasal passages, and the like, and may minimize damage to tissues and deterioration of the weight. FIG. 21 is an enlarged side view of an alternative embodiment 250 of the leading section of guide element 120. FIG. 21 also depicts an alternative embodiment 270 the insertion section of inserter element 130 which may advantageously be used in conjunction with the alternative leading section 250 of guide element 120. FIG. 22 is an enlarged cross-section view of the alternative leading section 250. FIG. 23 is an enlarged perspective view of the tip 272 of the alternative insertion section 270 of inserter element 130 portion of the alternative leading section 250 of guide element 120. The features of these FIGS. 21-23 will generally be described together. Except for the points of departure mentioned in connection with FIGS. 21-23, guide element 120 and inserter element 130 may be constructed in the same manner, and may have the same properties, as generally described earlier.

As best seen in FIGS. 21-22, alternative leading section 250 preferably has a slender longitudinal portion similar to that of leading section 154 (FIG. 1). Alternative leading section 250 preferably also has a body 252 which may include a first section 254 of generally cylindrical shape adjacent to a second section 258 of generally conical shape at a transition 262. The front or leading edge 256 of body 252 may have a rounded or partially-spherical contour to aid insertion.

It is not essential that the shape of the first section 254 be cylindrical, but it is preferable that it have sufficient diameter that the body 252 serve as a weight and be acted upon by the patient's swallowing mechanism, and it may be preferable that the contour be relatively free from large topological features that may interfere with anatomical structures during insertion. It is not essential that the shape of the second section 258 be conical, but is it preferable that its diameter gradually increase from that of the slender longitudinal portion of alternative leading section 250 to the full diameter of the body 252. The transition 262 from the first section 254 to the second section 258 may be so gradual as to be invisible, and these sections may be integrally constructed.

The body 252 is preferably securely attached to the slender longitudinal portion of alternative leading section 250 using an attachment structure 260. For example, the longitudinal portion of the alternative leading section 250 may extend into the body, and an attachment structure 260 may be formed as an anchor or other structure for securely mechanically engaging the body 252. However, the attachment structure 260 may also be formed as any part of leading section 250 in contact with body 252 and fastened thereto using any suitable fastening technology, including but not limited to glue, ultrasonic or chemical bonding or welding, structural features such as barbs or hooks, or a tight friction fit. The body 252 and the alternative leading section 250 may be constructed of materials and attached as described in connection with the swallowable weight 158 of the earlier-described embodiment.

As best seen in FIGS. 21 and 23, alternative insertion section 270 of inserter element 130 may include a relatively slender longitudinal portion 270 and a flared end portion 272 for engaging the body 252 of the swallowable weight of the alternative leading section 250 of guide element 130. The terminal end 276 of the flared end portion 272 may have a conical-concave shape to receive and engage the conical second section 258 of the alternative leading section 250 of the guide element 120. A slot extending along the dorsal surface of the alternative insertion section 270, formed by walls 280, and leading to a central lumen 282 forms a channel for receiving the longitudinal portion of alternative leading section 250, similar in structure and operation to channel 194 of insertion section 174 (FIG. 13). Although slot 270 and central lumen 282 are shown as separate structures, they could also be formed as an integral U-shaped channel or any other appropriate structure for receiving the longitudinal portion of alternative leading section 270.

It is not essential that the shape of the terminal end 276 exactly mate with the second section 258 of alternative leading section 250, but it is important that the shape be compatible so that when light tension is provided on guide element 120, the body 252 of the alternative leading section 250 is retained on the end of the alternative insertion section 270, and when such tension is released, the body 252 of the alternative leading section falls away. The alternative leading section 250 may be constructed of materials as described in connection with leading section 174 the earlier-described embodiment.

While the principles of the invention have been described above in connection with specific apparatus and applications, it is to be understood that this description is only an example and is not intended as a limitation on the scope of the invention. The above-described embodiments of the invention are merely examples of ways in which the invention may be carried out. Other ways may also be possible, and are within the scope of the following claims defining the invention.

What is claimed is:

1. A nasogastric tube insertion system for inserting a nasogastric tube in a human patient comprising:
    a guide element for insertion into the patient's stomach with a swallowable weight affixed to an end of a thin elongate element;
    a nasogastric tube comprising a retaining structure adapted to slidably move along said thin elongate element of the guide element; and
    an inserter element adapted to engage the end of said guide element to enable insertion of said guide element through a patient's nasal passages and into the patient's oropharynx;
    wherein the inserter element comprises a curved insertion section which is configured to follow a curved insertion path through the nasal passages of the patient, wherein the curved insertion section is constructed with a curve that generally conforms to the anatomy of the patient's nasal passages and the curved insertion path;
    wherein the curved insertion section is adapted to be inserted, with the guide element, along the curved insertion path, through the patient's nasal passages, and to the patient's oropharynx to position the swallowable weight of the guide element in the patient's oropharynx;
    wherein the guide element is separately insertable into the patient's stomach prior to the nasogastric tube.

2. The nasogastric tube insertion system of claim 1 wherein said thin elongate element is constructed as a line having a single filament.

3. The nasogastric tube insertion system of claim 1 wherein said thin elongate element is constructed as a string.

4. The nasogastric tube insertion system of claim 1 wherein said swallowable weight comprises:
    an attachment structure affixed to said thin elongate element; and
    a resilient body substantially surrounding said attachment structure;
    wherein the resilient body has a space to receive a tip of the curved insertion section of the inserter element.

5. The nasogastric tube insertion system of claim 1 wherein said retaining structure comprises a generally tubular element attached to said nasogastric tube parallel to and near an insertion end thereof, said tubular element having an opening to adapted to receive an end of said guide element.

6. The nasogastric tube insertion system of claim 1 wherein said retaining structure comprises a generally tubular element attached to said nasogastric tube parallel to and near an insertion end thereof, said tubular element being adapted for slidable movement of said nasogastric tube along said guide element.

7. The nasogastric tube insertion system of claim 1 wherein said retaining structure comprises a lumen extending through said tube; said lumen opening to the exterior of said nasogastric tube at an aperture near an insertion end thereof, and said lumen opening to the exterior of said nasogastric tube at a second aperture spaced from said first aperture.

8. The nasogastric tube insertion system of claim 1 wherein said inserter element comprises:
    a slender elongate body attached to the curved insertion section; and
    a handle attached to the body near an end thereof opposite said curved insertion section.

9. The nasogastric tube insertion system of claim 8 wherein said insertion section has a curvatures in the range of 70 to 100 degrees of arc in the direction of said handle to conform to the anatomy of the patient's nasal passages and oropharynx.

10. The nasogastric tube insertion system of claim 8 wherein said tip has a reduced thickness, said tip being adapted for loose engagement with a swallowable weight of said guide element.

11. The nasogastric tube insertion system of claim 1, wherein the curved insertion section comprises a length that is sufficient for the curved insertion section to insert the guide element through the nasal passages and to the oropharyns of the patient and optionally into the oropharynx.

12. A nasogastric tube insertion system comprising:
    a guide element for insertion into a patient's stomach with a swallowable weight affixed to an end of a thin elongate element;
    a nasogastric tube comprising a retaining structure adapted to slidably move along said thin elongate element of the guide element;
    an inserter element adapted to engage the end of said guide element to enable insertion of said guide element through a patient's nasal passages and into the patient's oropharynx;
    wherein the guide element is adapted to releasably engage a tip of a curved insertion section of an inserter element;
    wherein the inserter element comprises a curved insertion section which is configured to follow a curved insertion path through the nasal passages of the patient, wherein the curved insertion section is constructed with a curve that generally conforms to the anatomy of the patient's nasal passages and the curved insertion path;
    wherein the guide element is adapted to be insertable, with the curved insertion section, along the curved insertion path, through the patient's nasal passages and to the patient's oropharynx to position the end of the guide element in the patient's oropharynx;
    wherein the guide element is separately insertable into the patient's stomach prior to the nasogastric tube.

13. The nasogastric tube insertion system of claim 12 wherein said swallowable weight comprises:
    an attachment structure affixed to said thin elongate element; and
    a resilient body substantially surrounding said attachment structure;
    wherein the resilient body has a space to receive the tip of the curved insertion section of the inserter element.

14. The nasogastric tube insertion system of claim 12 wherein said retaining structure comprises a generally tubular element attached to said nasogastric tube parallel to and near an insertion end thereof, said tubular element having an opening to adapted to receive an end of said guide element.

15. The nasogastric tube insertion system of claim 12 wherein said retaining structure comprises a lumen extending through said tube; said lumen opening to the exterior of said nasogastric tube at an aperture near an insertion end thereof, said aperture being adapted to receive an end of said guide element, and said lumen opening to the exterior of said nasogastric tube at a second aperture spaced from said first aperture.

16. A system for insertion of a nasogastric tube, the system comprising:
a guide element for insertion into a patient's stomach with a swallowable weight affixed to an end of a thin elongate element;
an inserter element adapted to engage the end of said guide element to enable insertion of said guide element through a patient's nasal passages and into the patient's oropharynx;
wherein the inserter element comprises a curved insertion section which is configured to follow a curved insertion path through the nasal passages of the patient, wherein the curved insertion section is constructed with a curve that generally conforms to the anatomy of the patient's nasal passages and the curved insertion path;
wherein the curved insertion section is adapted to be inserted, with the guide element, along the curved insertion path, through the patient's nasal passages, and to the patient's oropharynx to position the end of the guide element in the patient's oropharynx separately from the nasogastric tube, wherein the guide element is to be swallowed by the patient prior to insertion of the nasogastric tube.

17. The nasogastric tube insertion system of claim 16 wherein said swallowable weight comprises:
an attachment structure affixed to said thin elongate element; and
a resilient body substantially surrounding said attachment structure;
wherein the resilient body has a space to receive a tip of the curved insertion section of the inserter element.

18. The nasogastric tube insertion system of claim 16 wherein said inserter element comprises:
a slender elongate body attached to the curved insertion section; and
a handle attached to the body near an end thereof opposite said curved insertion section.

19. A method for inserting a nasogastric tube in a patient comprising the steps of
a. engaging an end of a guide element with a tip of a curved insertion section of an inserter element to aid in placing the end of the guide element through the patient's nasal passages and into the patient's orophaxynx, wherein the curved insertion section is configured to follow a curved insertion path through the nasal passages of the patient, wherein the curved insertion section is constructed with a curve that generally conforms to the anatomy of the patient's nasal passages and the curved insertion path, wherein the guide element comprises a thin elongate element with a swallowable weight at the end;
b. inserting the curved insertion section of the inserter element, with the guide element, along the curved insertion path, through the patient's nasal passages and to the patient's oropharynx to position the swallowable weight of the guide element in the patient's oropharynx;
c. releasing the end of the guide element from the inserter element;
d. causing the patient to swallow the swallowable weight of the guide element into the patient's stomach; and
e. inserting the nasogastric tube along the guide element into the patient's stomach after the step of causing the patient to swallow the swallowable weight of the guide element into the patient's stomach.

20. The method of claim 19, wherein step a. thereof further comprises the steps of:
engaging the swallowable weight of the guide element to the tip of the curved inseition section of the inserter element; and
inserting the curved insertion section of the inserter element and the swallowable weight through the patient's nasal passages and into the patient's oropharynx.

21. The method of claim 19, wherein step e. thereof includes the steps of:
threading an opposite end of the guide element through a retaining structure of the nasogastric tube; and
slidably moving the nasogastric tube along a path established by the guide element into the patient's stomach after the step of causing the patient to swallow the swallowable weight of the guide element into the patient's stomach.

22. The method of claim 19, wherein step a. thereof further comprises the steps of:
engaging the swallowable weight of the guide element to the tip of the curved insertion section of the inserter element; and
inserting the curved insertion section of the inserter element and the swallowable weight through the patient's nasal passages; and
further comprising the step of:
b1. advancing said swallowable weight into said patient's oropharynx.

23. The method of claim 22 wherein step b1. further comprises advancing said swallowable weight into said patient's oropharynx by applying to said guide element gentle longitudinal pressure in the direction of said patient's oropharynx.

24. The method of claim 19, wherein step a. thereof further comprises the steps of:
engaging a swallowable weight affixed to said end of the guide element to the tip of the curved insertion section of the inserter element;
applying light tension to an opposite end of the guide element to retain the swallowable weight on the tip of the inserter element; and
inserting the curved insertion section of the inserter element and the swallowable weight through the patient's nasal passages and into the patient's oropharynx.

25. The method of claim 19, wherein step b. thereof includes releasing tension on an opposite end of the guide element to release the swallowable weight from the inserter element.

26. The method of claim 19, further comprising the step of:
removing the inserter element after releasing the end of the guide element from the inserter element.

27. The method of claim 26, wherein the step of removing the inserter element comprises the step of:
removing the inserter element after causing the patient to swallow the swallowable weight of the guide element into the patient's stomach.

28. The method of claim 19, further comprising the step of:
removing the nasogastric tube and the guide element together from the patient's stomach.

29. The method of claim 21, wherein the step of slidably moving comprises the step of:
sliding the retaining structure of the nasogastric tube over the guide element, wherein the nasogastric tube follows the path established by the guide element into the patient's stomach.

30. A method for inserting a nasogastric tube in a patient comprising the steps of:
  inserting a curved insertion section of an inserter element along a curved insertion path through the patient's nasal passages and towards the patient's oropharynx while the curved insertion section is engaged with a guide element, wherein the curved insertion path generally conforms to the anatomy of the patient's nasal passages, wherein the curved insertion section is constructed with a curve which follows the curved insertion path;
  disengaging the guide element from the inserter element, wherein the guide element comprises a swallowable weight affixed to a first end of a thin elongate element;
  causing the patient to swallow the swallowable weight into the patient's stomach to establish a desired path through the patient's nasal passages to the patient's stomach by the guide element;
  sliding the nasogastric tube over the guide element and along the desired path through the patient's nasal passages to the patient's stomach, after the step of causing the patient to swallow the swallowable weight into the patient's stomach.

31. The method of claim 30, further comprising the step of:
  engaging the swallowable weight of the guide element with a tip of the curved insertion section before inserting the curved insertion section of the inserter element.

32. The method of claim 30, further comprising the step of:
  applying light tension to a second end of the thin elongate element to retain the swallowable weight on the tip of the inserter element.

33. The method of claim 30, further comprising the step of:
  advancing the swallowable weight into the patient's oropharynx by sliding the guide element along the inserter element.

34. The method of claim 30, further comprising the step of:
  threading a second end of the thin elongate element through a guide element retaining structure of the nasogastric tube before sliding the nasogastric tube over the thin elongate element, wherein the guide element retaining structure is located at a distal end of the nasogastric tube.

35. The method of claim 30, wherein the step of sliding the nasogastric tube comprises the step of:
  telescoping the guide element through an aperture at a distal end of the nasogastric tube.

36. The method of claim 30, further comprising the step of:
  removing the nasogastric tube and the guide element together from the patient's stomach.

* * * * *